United States Patent
Oh et al.

(10) Patent No.: US 7,101,458 B2
(45) Date of Patent: Sep. 5, 2006

(54) PLASMA PROCESSING METHOD AND APPARATUS

(75) Inventors: Hin Oh, Nirasaki (JP); Yuichi Mimura, Nirasaki (JP)

(73) Assignee: Tokyo Electron Limited, Tokyo (JP)

( * ) Notice: Subject to any disclaimer, the term of this patent is extended or adjusted under 35 U.S.C. 154(b) by 199 days.

(21) Appl. No.: 10/727,604

(22) Filed: Dec. 5, 2003

(65) Prior Publication Data

US 2004/0200718 A1 Oct. 14, 2004

(30) Foreign Application Priority Data

Dec. 5, 2002 (JP) ............... 2002-353452

(51) Int. Cl.
*H01L 21/00* (2006.01)
*C23C 16/00* (2006.01)

(52) U.S. Cl. ............... 156/345.25; 156/345.24; 156/345.26; 156/345.27; 156/345.28; 118/708; 118/712; 204/192.33; 204/298.32

(58) Field of Classification Search ........... 156/345.24, 156/345.25, 345.26, 345.27, 345.28; 118/712, 118/708; 216/59, 60; 356/316; 250/339.07; 204/192.13, 298.32, 192.33, 298.33
See application file for complete search history.

(56) References Cited

U.S. PATENT DOCUMENTS

| | | | |
|---|---|---|---|
| 5,288,367 A | * | 2/1994 | Angell et al. ............... 216/60 |
| 6,521,080 B1 | * | 2/2003 | Balasubramhanya et al. ............... 156/345.24 |
| 2003/0055610 A1 | * | 3/2003 | Webber ............... 702/194 |

* cited by examiner

*Primary Examiner*—Ram N Kackar
(74) *Attorney, Agent, or Firm*—Oblon, Spivak, McClelland, Maier & Neustadt, P.C.

(57) ABSTRACT

In a plasma processing method and apparatus for monitoring an operating status of a plasma processing apparatus and/or a processing status of an object being processed, emission spectra emitted from a plasma is obtained as optical data when the plasma process is performed on the object. Quantitative data of each emission source is obtained from the obtained optical data by using reference data in a database storing therein emission spectra of a plurality of emission source as the reference data. The operating status of the plasma processing apparatus and/or the processing status of the object being processed is estimated based on changes in the quantitative data of each emission source.

8 Claims, 10 Drawing Sheets

PLASMA PROCESSING METHOD AND APPARATUS

FIELD OF THE INVENTION

The present invention relates to a plasma processing method and apparatus; and, more particularly, to a plasma processing method and apparatus for monitoring for example an operating status of the apparatus and a processing status of an object being processed, based on an analysis result of light emitted by a plasma.

BACKGROUND OF THE INVENTION

A conventional plasma processing apparatus for performing a plasma process such as an etching process on an object, e.g., a semiconductor wafer, to be processed, detects intensities of lights emitted from a plasma generated during the etching process, thereby monitoring an operating status of the apparatus or a processing status of the processed object. For example, there is disclosed a technique for monitoring the processing status of the object being processed, e.g., an end point detection of etching (see, e.g., Japanese Patent Laid-Open Publication No. H5-29276).

Such technique monitors emission intensities of activated species of process gas and reaction product emitted during a plasma process, to thereby detect the end point of the etching based on a ratio of the luminous intensities of two wavelengths. In other words, when the etching is completed due to the depletion of objects to be etched, the amount of activated species of process gas that contributes to the reaction starts increasing, and so does the emission intensity of the activated species of process gas. In contrast, since the amount of reaction products is comparatively reduced, the emission intensity thereof is also decreased. Based thereon, changes in the ratio of the emission intensity of process gas to that of reaction product are detected, thereby enabling an accurate end point detection of the etching.

Recently, as semiconductor devices becomes more compact, holes formed in a semiconductor wafer, for example, are also required to have a smaller opening ratio. However, monitoring the changes in the emission intensities of only two wavelengths of the activated species of process gas and the reaction products as described above is not sufficient to improve the accuracy of detecting the processing status, e.g., the end point detection of the etching.

Further, in case a noise is mixed in a sensor for detecting changes in the emission intensities of wavelengths in plasma, it is difficult to accurately detect the end point of the etching and estimate whether or not the plasma is stable in a processing chamber of the plasma processing apparatus, thereby deteriorating the accuracy of estimating a processing status of an object being processed or an operating status of a semiconductor manufacturing apparatus.

SUMMARY OF THE INVENTION

It is, therefore, an object of the present invention to provide a plasma processing method and apparatus capable of improving the accuracy of estimating an operating status of the apparatus and a processing status of an object being processed.

In accordance with one aspect of the invention, there is provided a plasma processing method for monitoring an operating status of a plasma processing apparatus and/or a processing status of an object being processed, based on a result of analyzing light emitted from a plasma generated while the plasma processing apparatus performs a plasma process on the object in a processing chamber, the plasma processing method including the steps of: obtaining an emission spectrum emitted from the plasma as optical data when the plasma process is performed on the object; obtaining quantitative data of each emission source from the obtained optical data by using reference data in a database storing therein emission spectra of a plurality of emission sources as the reference data; and estimating the operating status of the plasma processing apparatus and/or the processing status of the object being processed, based on changes in the quantitative data of each emission source.

In accordance with another aspect of the invention, there is provided a plasma processing apparatus for monitoring an operating status of a plasma processing apparatus and/or a processing status of an object being processed, based on a result of analyzing light emitted from a plasma generated while the plasma processing apparatus performs a plasma process on the object in a processing chamber, the plasma processing apparatus including: a unit for obtaining an emission spectrum emitted from the plasma as optical data when the plasma process is performed on the object; a unit for obtaining quantitative data of each emission source from the obtained optical data by using reference data in a database storing therein emission spectra of a plurality of emission sources as the reference data; and a unit for estimating the operating status of the plasma processing apparatus and/or the processing status of the object being processed, based on changes in the quantitative data of each emission source.

In accordance with the method and the apparatus of the present invention described above, since reference data including emission spectra of a plurality of emission sources are used, it is possible to check an end point of etching and estimate whether or not the plasma is stable in the processing chamber of the plasma processing apparatus, based on data of wider wavelengths compared with a case merely using data of specific wavelengths. Thus, in case semiconductor devices require finer processing performance, e.g., when a hole of a smaller opening ratio is formed on a semiconductor wafer, it is possible to accurately check the end point of the etching and estimate whether or not the plasma is stable in the processing chamber of the plasma processing apparatus, thereby improving the accuracy of monitoring the operating status of the plasma processing apparatus and the processing status of the object being processed.

Further, since the determination on the etching end point and/or the plasma stability is practiced based on each of the quotation data obtained by separating the optical data including emission spectra of each emission source, even though, e.g., a background noise generated by natural light or a noise generated by effects of a dark current in a charge coupled device (CCD) sensor for detecting plasma light is mixed in the optical data, it is possible to estimate the operating status of the plasma processing apparatus and the processing status of the object being processed without being affected by such noises. As a result, it is also possible to improve the accuracy of monitoring the operating status of the plasma processing apparatus and the processing status of the object being processed.

Further, since the operating status of the plasma processing apparatus is estimated based on the quantitative data of each emission source, which are obtained by separating emission spectra (reference data) stored in a database by using an emission spectrum (optical data) emitted from the plasma during a plasma process, it is possible to estimate the operating state of the plasma processing apparatus and the processing state of the object being processed in real time.

In the above-described method and apparatus, the database may be created in advance by obtaining as optical data the emission spectrum emitted from the plasma during the plasma process performed under multiple process conditions, and separating the optical data into emission spectra of a plurality of emission sources by a multivariate analysis and storing the emission spectra of each emission source as reference data. The multivariate analysis is an independent component analysis, and the emission spectra thereof correspond to independent components obtained by the independent component analysis. Furthermore, the number of independent components obtained by the independent component analysis is preferably greater than or equal to the number of process gas species used in the plasma process.

Since the optical data are separated into the emission spectra of each emission source, the database can be created without being affected by a noise even if the noise is mixed in the optical data. Especially, the effects of the noise can be more effectively removed by using the independent component analysis.

In an actual plasma process, even if a single process gas is used for generating a plasma, other emission sources may be generated and mixed therewith due to, e.g., a reaction in the processing chamber. Thus, it is difficult to directly detect emission spectra of each emission source by using, e.g., an optical measurement device. In contrast, with the present invention, it is possible to obtain emission spectra of each emission source, which are hardly obtained by a direct measurement of the emission spectra, by setting independent components obtained by the independent component analysis as reference data of the emission spectra.

Furthermore, in the above-described method and apparatus, the database may be created by a separate database creating unit other than a plasma processing apparatus for performing the actual plasma process. Accordingly, a separate plasma processing apparatus can perform such time-consuming processes as a processing of training wafers required for creating the database and a processing of the independent component analysis, thereby reducing burdens of the plasma processing apparatus. Moreover, since same database can be applied to every plasma processing apparatus which performs under same processes conditions, burdens of creating the database can be considerably reduced.

In the above-described method and apparatus, the quantitative data of each emission source may be obtained by determining inner product values between the optical data of the emission spectrum obtained by the plasma process and the reference data of each emission source stored in the database and defining the inner product values as the quantitative data of each emission source. Since it is possible to check the end point of the etching and estimate whether or not the plasma is stable by merely monitoring changes in the inner product values, the operating status of the apparatus and the processing status of the object being processed can be more simply and accurately monitored.

In the above-described method and apparatus, it may be estimated that the operating status of the plasma processing apparatus is stable when the quantitative data of each emission source become stable after the plasma processing apparatus performs the plasma process. Accordingly, it is possible to more simply and accurately estimate whether or not the plasma in the processing chamber is stable.

In the above-described method and apparatus, a completion of the plasma process for the object being processed may be estimated based on changes in the quantitative data of each emission source. As a result, it is possible to more simply and accurately check an end point of etching, for example.

BRIEF DESCRIPTION OF THE DRAWINGS

The above and other objects and features of the present invention will become apparent from the following description of preferred embodiments, given in conjunction with the accompanying drawings, in which.

DETAILED DESCRIPTION OF THE PREFERRED EMBODIMENTS

Hereinafter, a plasma processing apparatus in accordance with a preferred embodiment of the present invention will be described in detail with reference to the accompanying drawings. Further, in this specification and the accompanying drawings, like reference numerals will be given to like parts having substantially same functions, and redundant description thereof will be omitted.

(Configuration of the Plasma Processing Apparatus)

Figure 1:
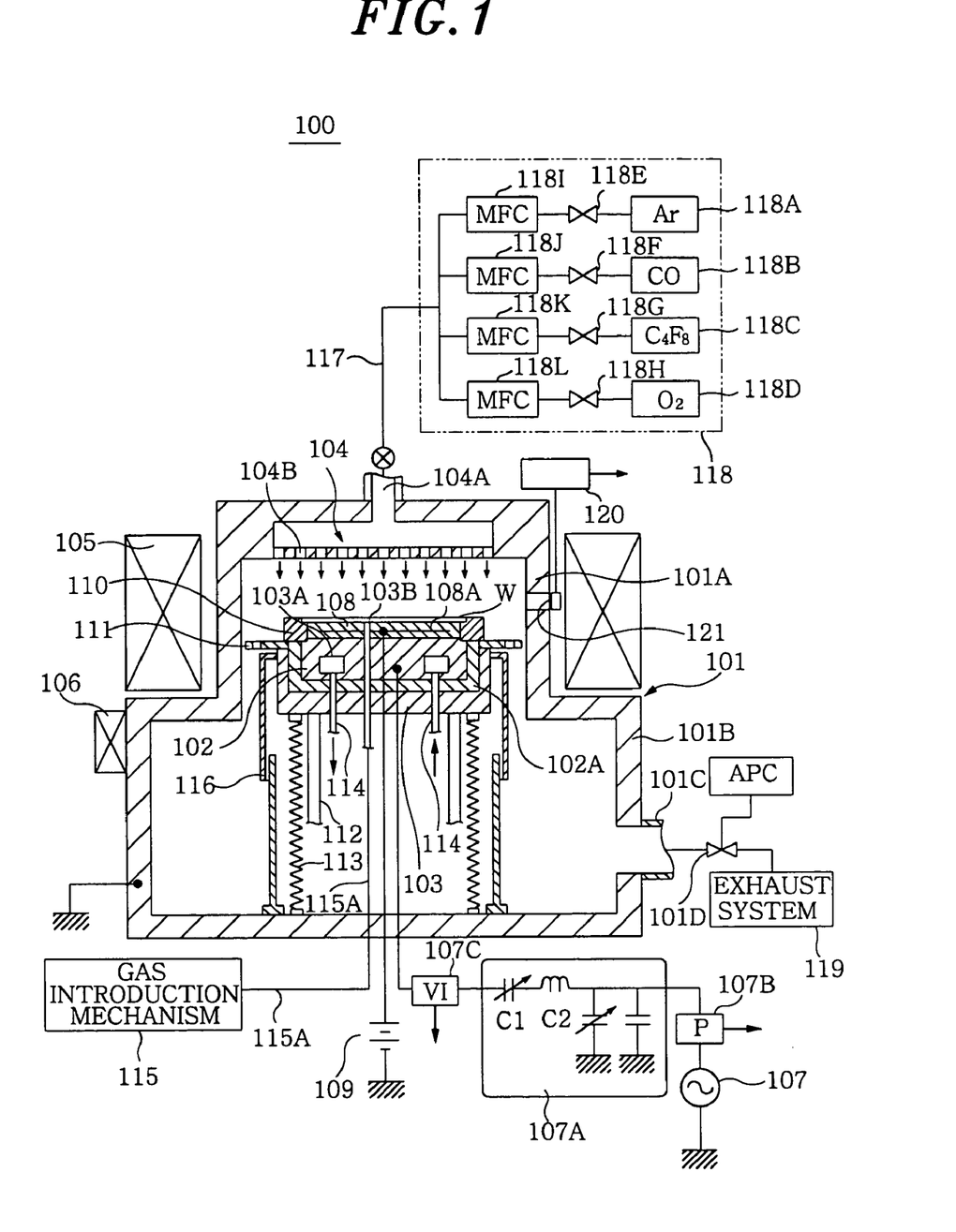
FIG. 1 shows a schematic diagram of a plasma processing apparatus in accordance with a preferred embodiment of the present invention.

FIG. 1 shows a schematic diagram of a plasma processing apparatus 100 in accordance with the preferred embodiment of the present invention. The plasma processing apparatus 100 includes a processing chamber 101 made of, e.g., aluminum; a vertically movable support 103 made of, e.g., aluminum, for supporting a lower electrode 102 installed in the processing chamber 101 via an insulating material 102A; and a shower head 104 installed above the support 103, for providing a process gas and serving as an upper electrode.

The processing chamber 101 has an upper room 101A having a smaller diameter and a lower room 101B having a larger diameter. The upper room 101A is surrounded by a dipole ring magnet 105. The dipole ring magnet 105 is formed by accommodating a plurality of columnar anisotropic segment magnets in a ring-shaped casing made of a magnetic substance and generates a horizontal magnetic field directed in one direction in the upper room 101A as a whole.

An opening for loading and unloading a wafer W into and from the processing chamber 101 is provided at an upper portion of the lower room 101B, and a gate valve 106 is installed thereat. Further, the lower electrode 102 is connected to a high frequency power supply 107 via an matching circuit 107A. A high frequency power P of 13.56 MHz is applied from the high frequency power supply 107 to the lower electrode 102, thereby forming a vertical electric field between the upper electrode 104 and the lower electrode 102 in the upper room 101A. The high frequency power P is detected by a power meter 107B connected between the high frequency power supply 107 and the matching circuit 107A. The high frequency power P is a controllable parameter. The high frequency power P and other controllable parameters, such as a flow rate of gas and a pressure in the processing chamber 101, which will be described later, are defined as control parameters in the present invention.

Moreover, an electrical measuring equipment (e.g., a VI probe) 107C is provided on the lower electrode 102 side (a high frequency voltage output side) of the matching circuit 107A. A high frequency voltage V, a high frequency current I, a high frequency power P and an impedance Z of fundamental and harmonic wave are detected as VI probe data based on a plasma generated in the upper room 101A by the high frequency power P applied to the lower electrode 102 through the electrical measuring equipment 107C.

Furthermore, the matching circuit 107A incorporates therein, e.g., two variable capacitors C1 and C2, a capacitor C, and a coil L, thereby performing impedance matching via the variable capacitors C1 and C2.

An electrostatic chuck 108 is disposed on a top surface of the lower electrode 102, and an electrode plate 108A of the electrostatic chuck 108 is connected to a DC power supply 109. Therefore, by applying a high voltage from the DC power supply 109 to the electrode plate 108A under a high vacuum state, the electrostatic chuck 108 electrostatically suctions a wafer W.

A focus ring 110 positioned around a periphery of the lower electrode 102 serves to focus the plasma generated in the upper room 101A on the wafer W. Further, an exhaust ring 111 installed on top of the support 103 is provided under the focus ring 110. The exhaust ring 111 has a plurality of holes spaced apart from each other at regular intervals in a circumferential direction thereof, and gases in the upper room 101A are discharged to the lower room 101B through the holes.

The support 103 is vertically movable between the upper room 101A and the lower room 101B through a ball screw mechanism 112 and a bellows 113. Thus, in case the wafer W is to be placed on the lower electrode 102, the lower electrode 102 is lowered into the lower room 101B by the support 103 and the gate valve 106 is opened so that the wafer W can be placed on the lower electrode 102 through a transfer mechanism (not shown).

Further, the support 103 has therein a coolant path 103A connected to a coolant line 114. By circulating coolant within the coolant path 103A through the coolant line 114, the wafer W is controlled to be maintained at a certain temperature. In addition, a gas path 103B is formed through the support 103, the insulating material 102A, the lower electrode 102, and the electrostatic chuck 108. Therefore, e.g., a He gas serving as a backgas can be supplied under a certain pressure from a gas introduction mechanism 115 to a fine gap formed between the electrostatic chuck 108 and the wafer W through a gas line 115A. Accordingly, thermal conductivity between the electrostatic chuck 108 and the wafer W can be increased. A reference numeral 116 indicates a bellows cover.

Provided in a top wall of the shower head 104 is a gas introduction portion 104A connected to a process gas supply system 118 through a line 117. The process gas supply system 118 includes an Ar gas source 118A, a CO gas source 118B, a $C_4F_8$ gas source 118C, and an $O_2$ gas source 118D. Such gas sources 118A to 118D supply corresponding gases of predetermined flow rates to the shower head 104 through valves 118E, 118F, 118G, and 118H and mass flow controllers 118I, 118J, 118K, and 118L, respectively. Then, the supplied gases are mixed together in the shower head 104 to form a mixture gas of a predetermined mixing ratio.

A plurality of holes 104B are regularly distributed in a bottom wall of the shower head 104. The mixture gas is supplied as a process gas from the shower head 104 into the upper room 101A through the holes 104B. Further, an exhaust pipe 101C is connected to an exhaust hole formed at a lower portion of the lower room 101B. By exhausting the processing chamber 101 through an exhaust system 119 implemented by, e.g., a vacuum pump connected to the exhaust pipe 101C, a predetermined gas pressure can be maintained in the processing chamber 101. The exhaust pipe 101C is provided with an APC (Automatic Performance Control) valve 101D, and an opening degree of the APC valve 101D is automatically regulated depending on the gas pressure in the processing chamber 101.

Moreover, a detection window 121 for detecting light generated in the processing chamber 101 is provided in, e.g., a sidewall of the upper room 101A. Installed immediately outside of the detection window 121 is a spectrometer 120 (hereinafter, referred to as the 'optical measurement device') for detecting plasma emission generated in the processing chamber 101. The optical measurement device 120 is configured to detect an emission spectrum of wavelength band ranging from about 200 nm to 730 nm from the plasma light emitted in the processing chamber 101 through the detection window 121. In the preferred embodiment, the emission spectrum of the wide wavelength band obtained by the optical measurement device 120 is used as optical data. Further, based on an analysis result of the optical data, e.g., a status of the plasma is monitored, thereby estimating whether or not the plasma is stable or checking an end point of the plasma process.

(Configuration of a Multivariate Analysis Unit)

Figure 2:
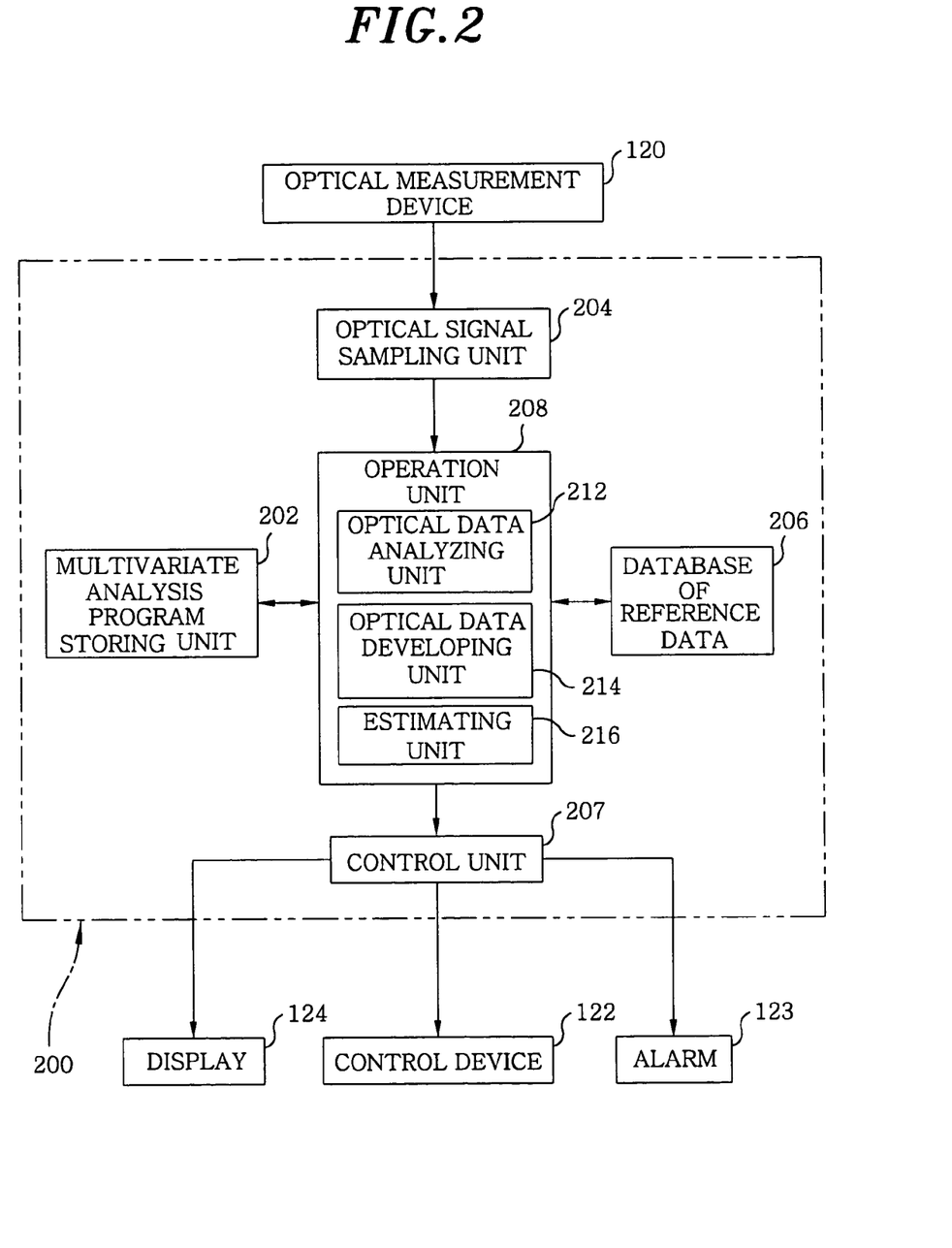
FIG. 2 illustrates a block diagram of an exemplary multivariate analysis unit in the preferred embodiment.

Hereinafter, a multivariate analysis unit incorporated in the plasma processing apparatus 100 in accordance with the preferred embodiment will be described with reference to the accompanying drawings. As illustrated in FIG. 2, a multivariate analysis unit 200 includes a multivariate analysis program storing unit 202 for storing multivariate programs such as an independent component analysis ("ICA") and an optical signal sampling unit 204 for intermittently sampling signals from the optical measurement device 120. The data sampled by the optical signal sampling unit 204 serve as detection values from the optical measurement device 120. The optical measurement device 120 detects light of 715 wavelengths at 0.7 nm intervals among wavelengths ranging from 200 nm to 730 nm, for example.

The plasma processing apparatus 100 includes a database of reference data 206 for storing as reference data emission spectra of respective emission sources to be described later; an operation unit 208; and a control unit 207 for controlling the plasma processing apparatus 100 based on operation signals from the operation unit 208. The operation unit 208 serves to develop optical data into quantitative data of the emission spectra of each emission source, based on the reference data stored in the database 206; and estimates, e.g., whether or not the plasma is stable or checks an end point of etching based on the quantitative data. The operation unit 208 sets a predetermined parameter or calculates an estimated value based on the result obtained by an estimating unit 216 thereof. The control unit 207 controls a completion of the plasma process performed by the plasma processing apparatus 100 in case the end point of the etching is estimated by the estimating unit 216.

Connected to the multivariate analysis unit 200 are a control device 122 for controlling the plasma processing apparatus 100, an alarm 123, and a display 124. The control device 122 continues to run or stops the processing of the wafer W based on signals from the control unit 207. In case the plasma is stable or the end point of etching is detected, the display 124 and the alarm 123 displays or alarms the state based on signals from the control unit 207.

The operation unit 208 has an optical data analyzing unit 212 for analyzing optical data obtained from the optical measurement device 120 when processing a training wafer into respective independent components (e.g., components of emission spectra of each emission source) by the multivariate analysis. Data of the respective independent components analyzed by the optical data analyzing unit 212 are stored as reference data in the database of reference data 206.

Furthermore, the operation unit 208 has an optical data developing unit 214 for developing optical data obtained from the optical measurement device 120 when an actual test wafer is processed, based on the respective independent components stored in the database of reference data 206; and the estimating unit 216 for estimating whether or not the plasma is stable or checking the end point of etching, based on variations in the developed data of the respective independent components.

(Process of the Optical Data Analyzing Unit)

The optical data analyzing unit 212 performs an independent component analysis (ICA) as a multivariate analysis, thereby separating the optical data into the independent components of emission spectra of the respective emission sources such as CO and $O_2$.

The ICA is a technique for separating signals by independency based on high-order statistics or temporal relations. To be specific, the technique is disclosed in, e.g., "Application of ICA to an acoustic processing" (Ikeda Shiro, Japanese Acoustic Institute Year 2000 Fall Research Paper, pp. 435–438, Iwate Prefectural University, September 2000).

Specifically, in the ICA, m-number of original signal data are represented in vector by the following equation 1-1:

$$s(t)=(s_1(t), s_2(t), \ldots, s_m(t))^T \quad \text{Eq. 1-1}$$

wherein t(t=0, 1, 2 . . . ) and T indicate time and transposition, respectively. Further, each component of s(t) averages 0 and is independent from each other.

At this time, observation signal data observed by n-number of sensors are expressed in vector by the following equation 1-2:

$$x(t)=(x_1(t), x_2(t), \ldots, x_n(t))^T \quad \text{Eq. 1-2}$$

Generally, the number of the original signal data, i.e., m, is not necessarily equal to that of sensors, i.e., n. However, in order to solve such problems, m must be smaller than or equal to n, i.e., $m \leq n$.

Here, a linear relationship is assumed by employing an m×n real number matrix A for a relation between s(t) and x(t), wherein the linear relationship is described as follows:

$$s(t)=Ax(t) \quad \text{Eq. 1-3.}$$

The ICA is to divide the observation signal data x(t) into n-pieces of independent signal components without having any prior knowledge on a configuration of a probability distribution of the original signal data s(t) and the matrix A. In other words, in case $n \leq m$, there exists a solution. Since an n×m real number matrix W exists, y(t) is obtained by the following Eq. 1-4:

$$y(t)=Wx(t) \quad \text{Eq. 1-4.}$$

Herein, in case WA is equal to $I_n$ indicating an n-th order unit matrix, i.e., $WA=I_n$, y(t) is equal to s(t). However, since a change in order and a size of components of y(t) do not affect independency, the randomness thereof is allowed.

The matrix W should be determined in order to calculate y(t). There have been proposed various solutions such as a solution based on the independency of a probability distribution and a solution based on a temporal structure.

For example, the solution based on the independency of the probability distribution is as follows: First, it is assumed that respective components $S_i(t)$ of the original signals follow a probability distribution instead of a normal distribution; but, the probability distribution is unknown. A simultaneous distribution density function of y(t) is represented as follows:

$$p(y)=p(y_1, y_2, \ldots, y_n) \quad \text{Eq. 2-1.}$$

If the observation signal x(t) can be accurately divided by the matrix W, respective components $y_i$ of y become independent, and the function P(y) can be expressed as follows:

$$p(y) = \prod_{i=1}^{n} p(y_i). \quad \text{Eq. 2-2}$$

Thus, the matrix W is determined in such a way that the left side and the right side of Eq. 2-2 are equal. The matrix W is obtained by using an evaluation function in such a manner that a Kullback-Leiber divergence (K-L divergence) between the left side and the right side of Eq. 2-2 is small, wherein a definition of the K-L divergence can be defined as follows:

$$KL(W) = \int p(y)\log\frac{p(y)}{\prod_{i=1}^{n} p(y_i)} dy \quad \text{Eq. 2-3}$$

$$= -H(Y;W) + \sum_{i=1}^{n} H(Y;W)$$

wherein H(Y ; W) and H($Y_i$ ; W) indicate an entropy of a simultaneous distribution and that of a marginal distribution, respectively. H(Y ; W) and H($Y_i$ ; W) can be expressed in terms of p(x) and the matrix W by the following equations 2-4 and 2-5, respectively:

$$H(Y;W)=H(X)+\log|W| \quad \text{Eq. 2-4}$$

$$H(Y_i;W)=-\int p(x)\log p(y_i)dx \quad \text{Eq. 2-5.}$$

KL(W) becomes 0 only if the respective components of p($y_i$) are independent from each other, on the assumption that the original signal data s(t) do not have a normal distribution. In order to determine the matrix W, a steepest descent method may be used after determining a gradient of KL(W) with respect to W. In other words, the matrix W is obtained by the following equations 2-6 and 2-7:

$$\Delta W a - \frac{\partial KL(W)}{\partial W} = (W^T)^{-1} - E_x[\varphi(y)x^T] \qquad \text{Eq. 2-6}$$
$$= (I - E_x[\varphi(y)y^T])(W^T)^{-1}$$

$$\varphi(y) = -\left(\frac{\partial \log p(y_1)}{\partial y_1}, \ldots, \frac{\partial \log p(y_n)}{\partial y_n}\right)^T. \qquad \text{Eq. 2-7}$$

Furthermore, a separation method based on the temporal structure, which is an alternative solution of the ICA, includes a method based on an autocorrelation function, for example. In this case, signals are to be ergodic, and spectrum densities of the respective original signal data are to be different from each other. Based on the independency of the original signal data, a correlation function of the observation data is expressed by the following equation 3-1:

$$\langle x(t)x(t+\tau)^T \rangle = A \langle s(t)s(t+\tau)^T \rangle A^T \qquad \text{Eq. 3-1}$$
$$= A \begin{pmatrix} R_{s_1}(\tau) & & 0 \\ & \ddots & \\ 0 & & R_{s_n}(\tau) \end{pmatrix} A^T.$$

The left side of Eq. 3-1 indicates an average in the probability distribution of x(t), and $R_{si}(\tau)$ represents the autocorrelation function of the original signal data. When the matrix W is accurately determined, the correlation function of y(t) is expressed by the following equation 3-2:

$$\langle y(t)y(t+\tau)^T \rangle = \langle WAs(t)(WAs(t+\tau))^T \rangle \qquad \text{Eq. 3-2}$$
$$= \begin{pmatrix} \lambda_{1'}^2 R_{s_{1'}}(\tau) & & 0 \\ & \ddots & \\ 0 & & \lambda_{n'}^2 R_{s_{n'}}(\tau) \end{pmatrix}.$$

In the equation 3-2, 1', 2', . . . , n' are to represent a randomness of a substitution and $\lambda_i$ is to express a randomness of a size. If each signal is completely independent without any noise, an optimum matrix W is expressed by a diagonal matrix for expressing the correlation function of y(t) for every τ, as shown in Eq. 3-2. Accordingly, the correlation function of X(t) is obtained based on a plurality of time differences $\tau_i$. At the same time, the matrix W can be obtained as the diagonal matrix.

(Order in Creation of Database)

Hereinafter, an order in creating the database 206 for storing emission spectra of the respective emission sources as reference data will be described. The creation of the database 206 is performed by the optical data analyzing unit 212.

First, the optical measurement device 120 measures plasma light generated by performing an experiment of an etching process by using a training set of wafers. In order to do so, 36 wafers (bare silicon) are prepared as the training set. The bare silicon is a wafer having Si throughout on an entire surface thereof. As for a standard etching condition, a high frequency power applied to the lower electrode 102 and a pressure in the processing chamber 101 were set to be respectively 1500 W and 40 mTorr. A process gas involved was a mixture gas of 10 sccm $C_4F_8$, 5 sccm $O_2$, 50 sccm CO, and 200 sccm Ar. Further, a gap formed between the upper electrode 104 and the wafer was 27 mm.

In this case, it is possible to efficiently set each parameter data by using an experiment design. In the preferred embodiment, each of training wafers is etched by varying each control parameter of an etching condition within a certain range from a corresponding standard value. Moreover, during the etching process, optical data for each training wafer are measured multiple times, and an average thereof is calculated.

Herein, values of the control parameters are changed within respective maximum variation ranges of the control parameters that can be encountered during the etching process. In the preferred embodiment, the high frequency power, the pressure in the processing chamber 101, the size of a gap formed between the upper electrode 104 and the lower electrode 102, and the flow rate of each component of the process gases (Ar, CO, $C_4F_8$, and $O_2$) are used as the control parameters. A standard value of each control parameter is determined depending on an object to be etched.

For instance, when the etching process is performed for each training wafer, each control parameter of every training wafer is changed within limits of level 1 and level 2 shown in the following Table 1, from the standard value of each control parameter. Further, while each training wafer is processed, the optical measurement device 120 measures as the optical data the intensities of emission spectrum of 715 wavelengths at 0.7 nm intervals among wavelengths ranging from about 200 nm to 730 nm for example.

TABLE 1

|  | Power W | Pressure mTorr | Gap mm | Ar Sccm | CO sccm | $C_4F_8$ sccm | $O_2$ Sccm |
|---|---|---|---|---|---|---|---|
| Level 1 | 1400 | 35 | 25 | 150 | 30 | 8 | 2 |
| Standard | 1500 | 40 | 27 | 200 | 50 | 10 | 5 |
| Level 2 | 1600 | 50 | 30 | 280 | 70 | 12 | 6 |

Prior to processing the training wafers, each control parameter is set as a standard value of bare silicon, and then 5 dummy wafers are processed under the standard condition to thereby stabilize the plasma processing apparatus 100. Next, 36 training wafers are etching-processed. At this time, each training wafer is processed by changing the value of each control parameter within the limits of level 1 and level 2 as illustrated in the following Table 2. L1 to L36 shown in Table 2 indicate numbers of the training wafers.

TABLE 2

|  | Power W | Pressure mTorr | Gap mm | Ar sccm | Co sccm | $C_4F_8$ sccm | $O_2$ Sccm |
|---|---|---|---|---|---|---|---|
| L1 | 1500 | 40 | 27 | 200 | 50 | 10 | 5 |
| L2 | 1500 | 42 | 25 | 170 | 64 | 10 | 4.5 |
| L3 | 1500 | 38 | 29 | 200 | 36 | 9.5 | 4.5 |
| L4 | 1500 | 40 | 27 | 230 | 64 | 9.5 | 3.5 |
| L5 | 1540 | 42 | 27 | 170 | 50 | 9.5 | 4.5 |
| L6 | 1460 | 38 | 25 | 170 | 36 | 9.5 | 3.5 |
| L7 | 1500 | 38 | 27 | 200 | 50 | 10 | 4 |
| L8 | 1540 | 38 | 25 | 230 | 50 | 10 | 3.5 |
| L9 | 1540 | 38 | 29 | 230 | 64 | 10.5 | 4.5 |
| L10 | 1460 | 42 | 29 | 200 | 64 | 10 | 3.5 |
| L11 | 1500 | 40 | 29 | 170 | 50 | 10.5 | 3.5 |
| L12 | 1540 | 40 | 25 | 200 | 64 | 9.5 | 4 |
| L13 | 1540 | 42 | 27 | 200 | 36 | 10.5 | 3.5 |

TABLE 2-continued

|     | Power W | Pressure mTorr | Gap mm | Ar sccm | Co sccm | $C_4F_8$ sccm | $O_2$ Sccm |
|-----|---------|----------------|--------|---------|---------|---------------|------------|
| L14 | 1500 | 42 | 25 | 230 | 36 | 10.5 | 4 |
| L15 | 1460 | 40 | 27 | 230 | 36 | 10 | 4.5 |
| L16 | 1460 | 40 | 25 | 200 | 50 | 10.5 | 4.5 |
| L17 | 1460 | 42 | 29 | 230 | 50 | 9.5 | 3.5 |
| L18 | 1500 | 40 | 27 | 200 | 50 | 10 | 4 |
| L19 | 1400 | 40 | 27 | 200 | 50 | 10 | 4 |
| L20 | 1600 | 40 | 27 | 200 | 50 | 10 | 4 |
| L21 | 1400 | 40 | 27 | 150 | 50 | 10 | 4 |
| L22 | 1500 | 45 | 27 | 200 | 50 | 10 | 4 |
| L23 | 1500 | 40 | 25 | 200 | 50 | 10 | 4 |
| L24 | 1500 | 40 | 30 | 200 | 50 | 10 | 4 |
| L25 | 1500 | 40 | 27 | 120 | 50 | 10 | 4 |
| L26 | 1500 | 50 | 27 | 200 | 50 | 10 | 4 |
| L27 | 1500 | 40 | 27 | 200 | 30 | 10 | 4 |
| L28 | 1500 | 40 | 27 | 200 | 70 | 10 | 4 |
| L29 | 1500 | 40 | 27 | 200 | 50 | 8 | 4 |
| L30 | 1500 | 40 | 27 | 200 | 50 | 12 | 4 |
| L31 | 1400 | 35 | 27 | 200 | 50 | 10 | 2 |
| L32 | 1600 | 50 | 27 | 200 | 50 | 10 | 6 |
| L33 | 1400 | 50 | 25 | 200 | 50 | 10 | 4 |
| L34 | 1600 | 50 | 30 | 200 | 50 | 10 | 4 |
| L35 | 1400 | 40 | 27 | 120 | 50 | 10 | 4 |
| L36 | 1600 | 40 | 27 | 280 | 50 | 10 | 4 |

The ICA of multiple optical data obtained from the optical measurement device 120 for each training wafer is performed, so that the optical data can be separated into a plurality of independent components. To be specific, spectra of the optical data for respective training wafers are set to be data 1 to data i, and the number of wavelengths of each optical data is set to be the number of sensors $\lambda$m. If the data 1 to data i and the number of sensors $\lambda$m are applied to x(t) of the equation 1-2, a result thereof is expressed by the following Eq. 4-1. In addition, time t is equivalent to the wafer number.

$$x(t) = (x_{\lambda 1}(t), x_{\lambda 2}(t), \ldots, x_{\lambda m}(t))^T \quad \text{Eq. 4-1}$$

$$= \begin{pmatrix} x_{\lambda 1}(1) & x_{\lambda 2}(1) & \cdots & x_{\lambda m}(1) \\ x_{\lambda 1}(2) & x_{\lambda 2}(2) & \cdots & x_{\lambda m}(2) \\ \vdots & \vdots & \vdots & \vdots \\ x_{\lambda 1}(i) & x_{\lambda 2}(i) & \cdots & x_{\lambda m}(i) \end{pmatrix}^T$$

$$= \begin{pmatrix} \text{spectrum of data 1} \\ \text{spectrum of data 2} \\ \vdots \\ \text{spectrum of data } i \end{pmatrix}^T.$$

Since the number of training wafers L1 to L36 and the number of wavelengths of the optical data are respectively 36 and 712 in the this embodiment, i and $\lambda$m are respectively 36 and 712 in the equation 4-1.

Furthermore, in the preferred embodiment, since WA is equal to $I_n$ ($I_n$ is an n-th order unit matrix), y(t) is equal to s(t). Accordingly, y(t) of Eq. 1-4 is expressed by the following Eq. 4-2:

$$s(t) = y(t) = (y_{\lambda 1}(t), y_{\lambda 2}(t), \ldots, y_{\lambda m}(t))^T \quad \text{Eq. 4-2}$$

$$= \begin{pmatrix} y_{\lambda 1}(1) & y_{\lambda 2}(1) & \cdots & y_{\lambda m}(1) \\ y_{\lambda 1}(2) & y_{\lambda 2}(2) & \cdots & y_{\lambda m}(2) \\ \vdots & \vdots & \vdots & \vdots \\ y_{\lambda 1}(i) & y_{\lambda 2}(i) & \cdots & y_{\lambda m}(i) \end{pmatrix}^T$$

$$= \begin{pmatrix} \text{independent component 1} \\ \text{independent component 2} \\ \vdots \\ \text{independent component } i \end{pmatrix}^T.$$

The independent components are determined by applying Eqs. 4-1 and 4-2 to Eq. 1-4 and obtaining the matrix W of Eq. 1-4 by the ICA. Moreover, the number of the independent components can be arbitrarily determined. However, in view of Eq. 1-4, the maximum number thereof needs to be less than or equal to i.

Figure 3:
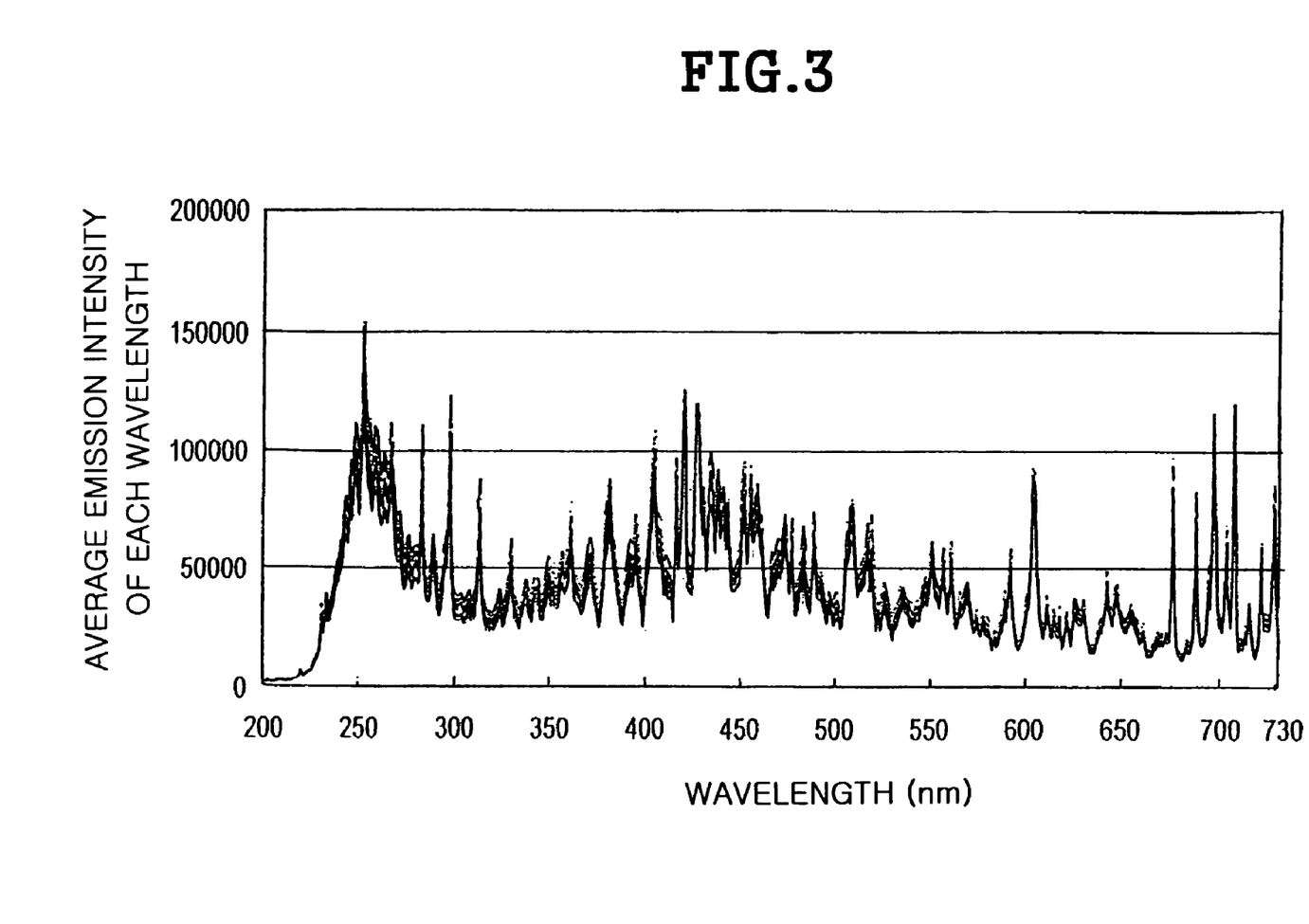
FIG. 3 provides a graph showing optical data of an emission spectrum of plasma, which are measured by an optical measurement device in the preferred embodiment.

Hereinafter, a result of analyzing the optical data into nine independent components by the ICA will be described with reference to the accompanying drawings. FIG. 3 provides a graph showing optical data of an emission spectrum of a plasma, which is measured by an optical measurement device before the ICA is performed. In FIG. 3, the X-axis and the Y-axis represent wavelengths and an average emission intensity of each wavelength, respectively. In the ICA, the optical data are regarded as a mixture of emission spectra of a plurality of independent emission sources.

Figure 4:
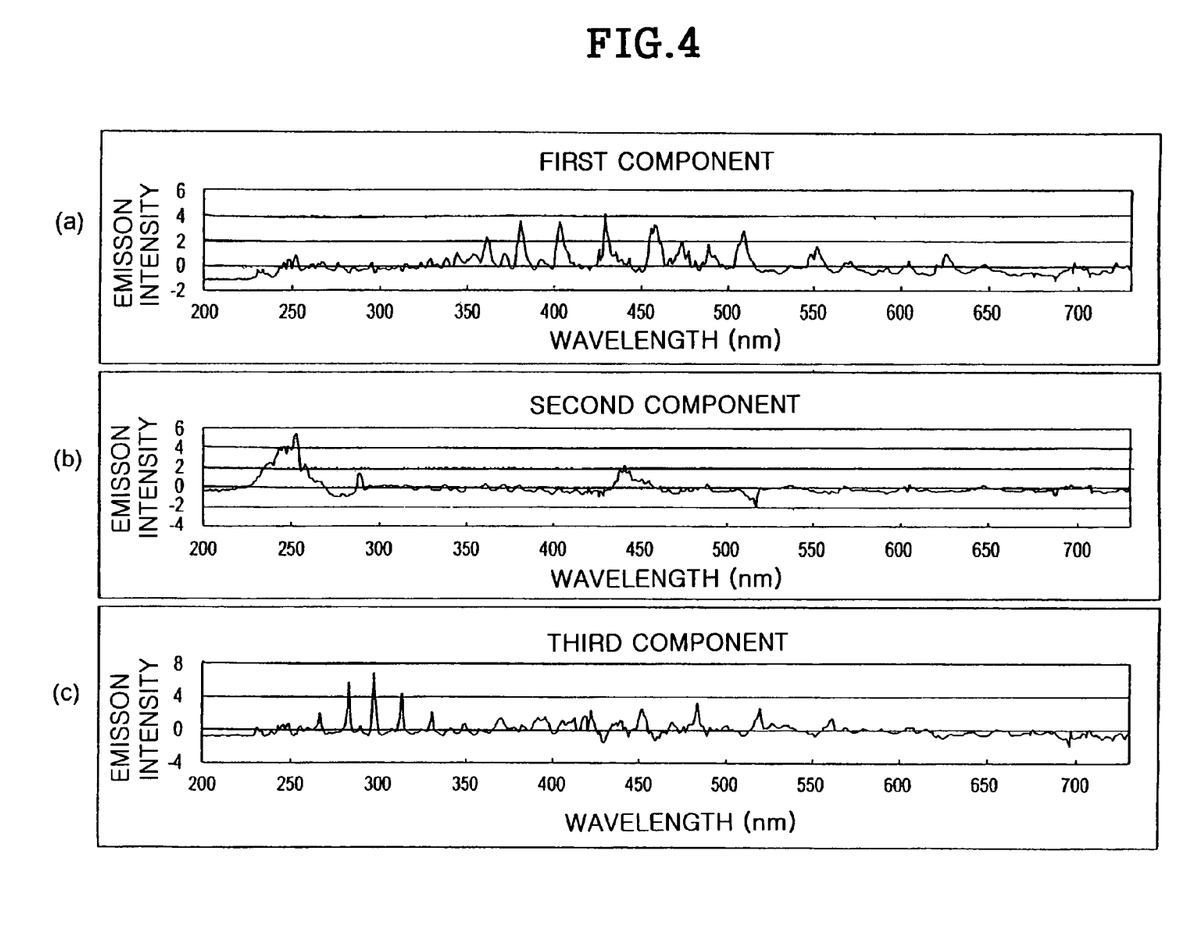
FIG. 4 presents graphs illustrating data of independent components in the preferred embodiment.
Figure 5:
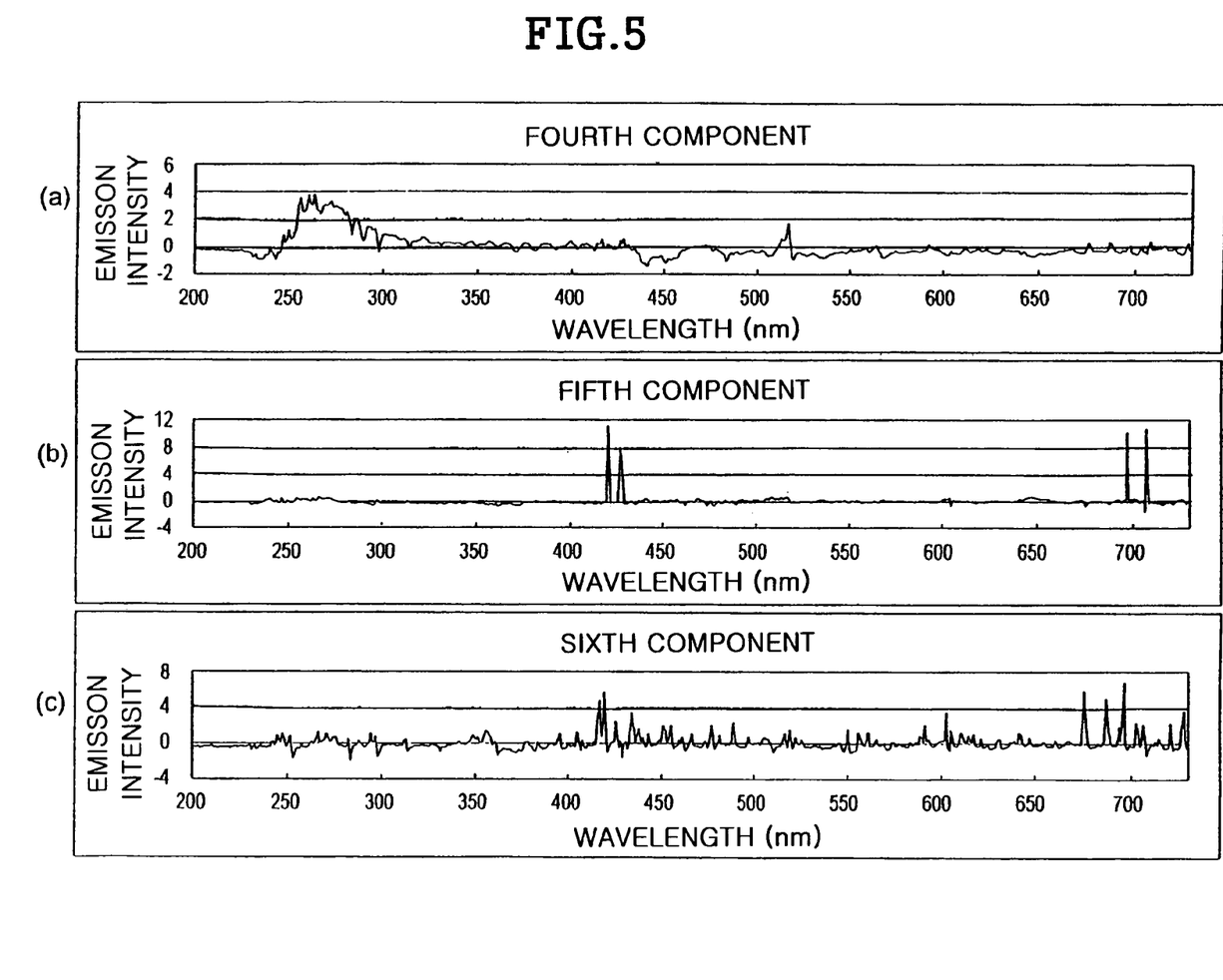
FIG. 5 represents graphs illustrating data of independent components in the preferred embodiment.
Figure 6:
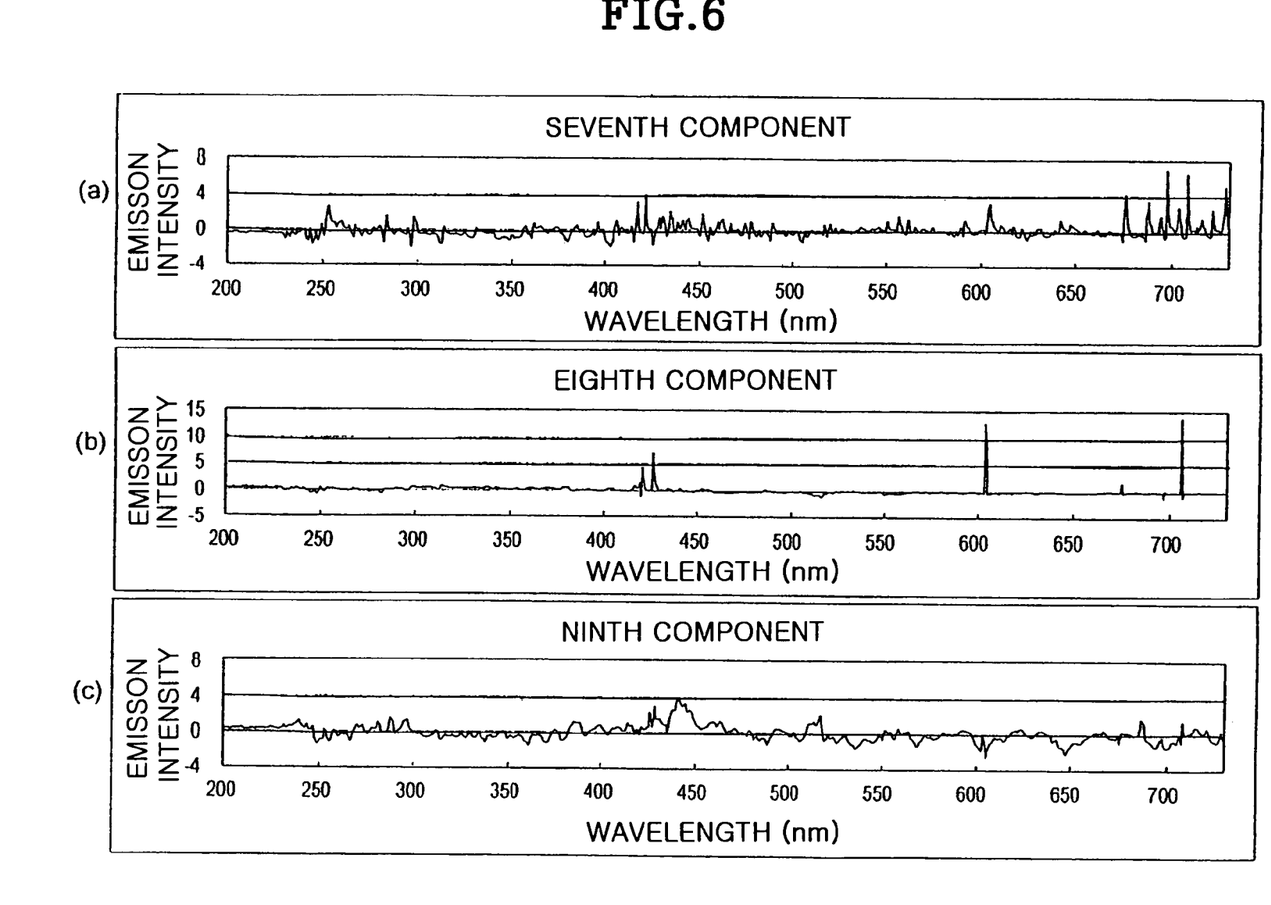
FIG. 6 depicts graphs showing data of independent components in the preferred embodiment.

FIGS. 4 to 6 depict a first to a ninth independent component obtained by performing the ICA to separate the optical data shown in FIG. 3 into the nine independent components. In FIGS. 4 to 6, the X-axis and the Y-axis represent wavelength and emission intensity, respectively.

The independent components are considered to correspond to the emission spectra of the emission sources, respectively. For example, the first to the third independent component shown in graphs (a) to (c) of FIG. 4 are considered corresponding to the emission spectra of the emission sources mainly related to $O_2$ gas, CF based gas and CO gas, respectively.

Figure 7:
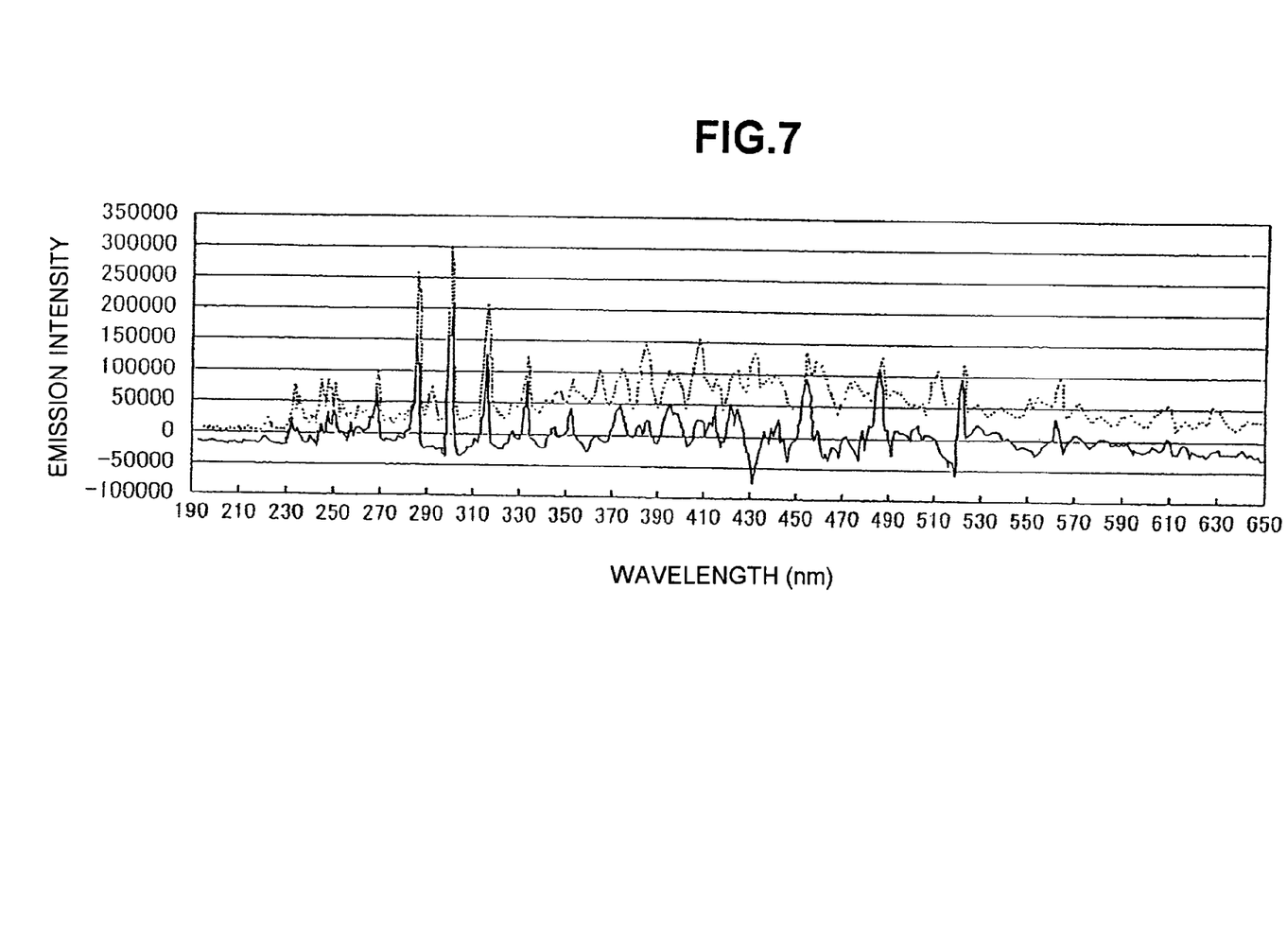
FIG. 7 describes a diagram for comparing data of an emission spectrum obtained by a plasma process using a known gas ($CO_2$) with a certain independent component.
Figure 8:
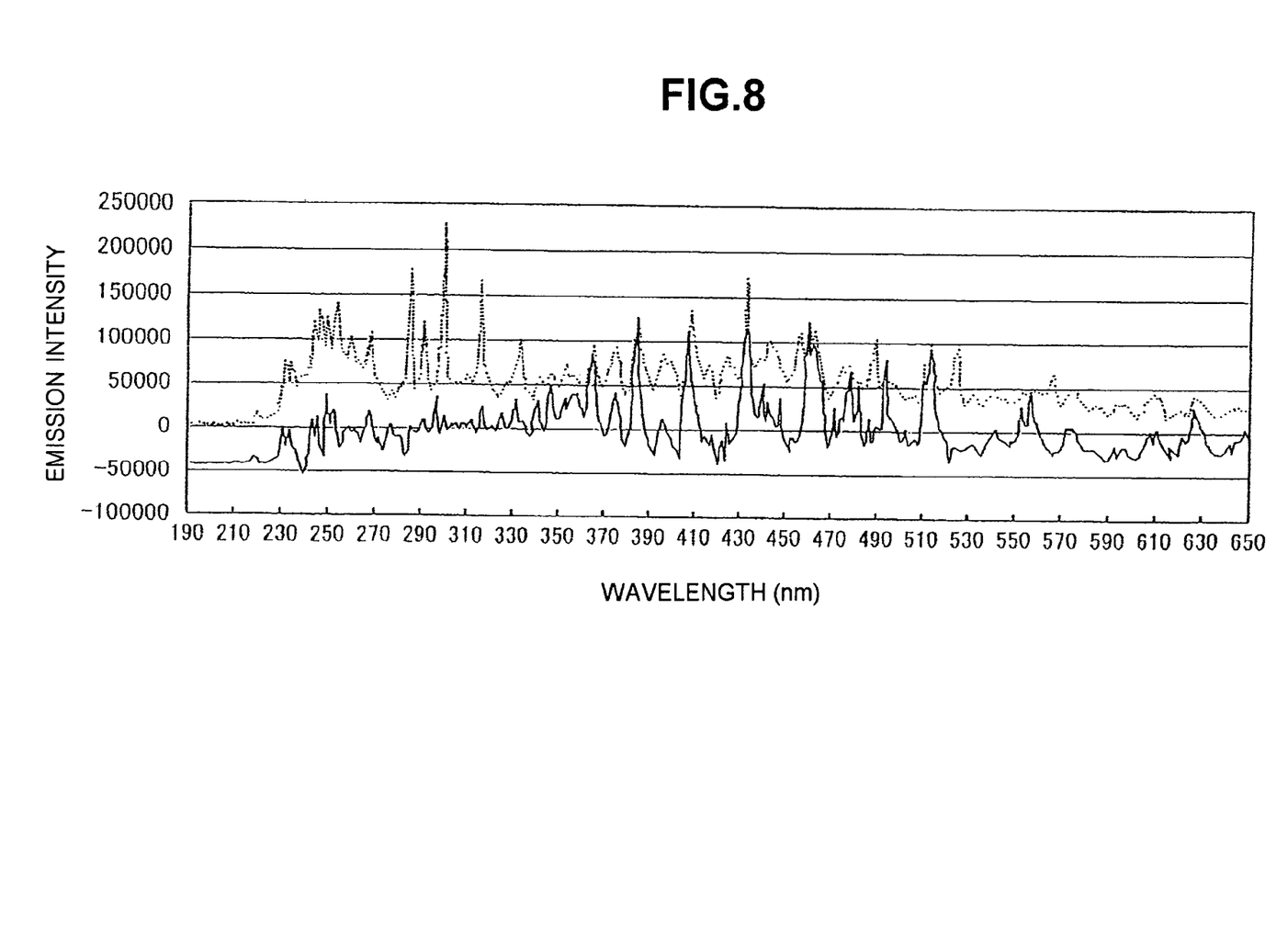
FIG. 8 offers a diagram for comparing data of an emission spectrum obtained by a plasma process using a known gas ($O_2$) with a certain independent component.

As another case where optical data obtained by performing a plasma process on a bare wafer is separated into eight independent components by the ICA, FIGS. 7 and 8 show graphs for comparing certain independent components thereof with data of the emission spectrum obtained by performing plasma processes by using known process gases. The dotted line shown in the graph of FIG. 7 indicate optical data obtained by performing the plasma process by using a $CO_2$ gas as a known process gas and the solid line shown therein is data of an independent component. The dotted line illustrated in the graph of FIG. 8 represents optical data obtained by performing the plasma process by using an $O_2$ gas as a known process gas. Further, the solid line depicted therein represents data of a different independent component.

Referring to FIG. 7, the data of $CO_2$ gas indicated by the dotted line and that of the independent component indicated by the solid line have approximately identical characteristics in the emission intensity and, therefore, are considered to have identical characteristics. For example, the data of $CO_2$ gas indicated by the dotted line show peaks at wavelengths ranging from about 280 nm to 320 nm, which are substantially identical to the data of the independent component.

As can be also seen from FIG. 8, the data of $O_2$ gas indicated by the dotted line and that of the independent component indicated by the solid line have approximately identical characteristics in the emission intensity. However, in FIG. 8, certain parts in the emission intensity of the $O_2$ gas data are different from those of the independent component data. For example, the $O_2$ gas data indicated by the dotted line show peaks at wavelengths ranging from about 280 nm to 320 nm, but the independent component data do not have peaks in that range. However, those peaks of the $O_2$ gas data shown in FIG. 8 are identical to those of the $CO_2$ gas data indicated by the dotted line in FIG. 7. Presumably, this is because, even if only the $O_2$ gas is used, the $CO_2$ gas is generated due to a reaction with carbon containing deposits produced by a plasma process.

Further, it can also be considered that the independent component obtained by the ICA corresponds to emission spectrum data of $O_2$ gas only. In other words, even if a known gas is used in the plasma process, other gases may be actually generated. Therefore, although it is difficult to detect only emission spectrum data of a emission source corresponding to a known gas even in a case of performing the plasma process by using the known gas only, it is possible to obtain the emission spectrum data thereof by using the ICA.

As described above, in the preferred embodiment, the independent components obtained by the ICA are considered to correspond to the emission spectra of the emission sources, respectively. Accordingly, each independent component obtained by performing the ICA on the optical data is stored in the database 206 as reference emission spectrum data of each emission source, thereby creating the database 206 having the emission spectra of the respective emission sources.

As described above, since the optical data in which the emission spectra of the respective emission sources are mixed are separated into the emission spectrum of each emission source, the database can be created without being affected by noises even if the noises are introduced in the optical data. Especially, by using the ICA, the effects of the noises can be more effectively removed.

Furthermore, even though a single process gas species is used for generating a plasma, other emission sources can be generated and mixed therewith due to, e.g., a reaction in the processing chamber during an actual plasma process, thereby making it difficult to directly detect the emission spectrum of each emission source by using, e.g., the use of the optical measurement device. In the present invention, however, the emission spectra of the respective emission sources, which can be hardly obtained by a direct measurement of the emission spectra, can be obtained by setting as reference data independent components obtained by performing the ICA on the optical data.

Moreover, the database of reference data 206 may store therein only a database created by using a different database creating unit, e.g., a separate plasma processing apparatus other than the plasma processing apparatus 100. In this way, the separate plasma processing apparatus can perform such time-consuming processes as the processing of training wafers required for creating database and the processing of independent component analysis, thereby reducing burdens of the plasma processing apparatus 100. In addition, since same database can be applied to every apparatus of a same kind performing a process under same process conditions, it is possible to considerably reduce burdens required to create the database. Moreover, the database of reference data 206 may also be created based on known data disclosed in the art on emission spectra of various emission sources.

(Process of Actual Wafers)

The following is a description of a method for monitoring an operating status of a plasma processing apparatus and a processing status of a wafer in case a plasma process is performed on an actual wafer to be used, e.g., in manufacturing semiconductor devices.

Whenever the actual wafer (hereinafter, referred to as the "test wafer") is plasma-processed by the plasma processing apparatus 100, the multivariate analysis unit 200 receives an emission spectrum of the plasma measured by the optical measurement device 120. With the optical signal sampling unit 204, the emission spectrum is obtained as optical data.

Further, the optical data developing unit 214 of the operation unit 208 develops the optical data by using the reference data of the database 206. The optical data developing unit 214 separates the optical data into quantitative data of emission spectra of the respective emission sources by using the reference data of the emission spectra of the emission sources, the reference data being independent components stored in the database 206.

Specifically, inner product values between the optical data of the emission spectrum obtained by the plasma process and the reference data of the respective emission sources stored in the database 206 are calculated. Then, each of the inner product value is set as quantitative data of the corresponding emission source. For example, a wafer (t=0) is plasma-processed, and optical data involved are defined as x(0) to be expressed by the following equation 5-1. In order to obtain the quantitative data of an independent component 1 (related to, e.g., $O_2$) for x(0), an inner product value P(0) between the optical data x(0) and y(0) expressed by the following equation 5-2 is calculated, wherein y(0) indicates the independent component 1 stored in the database 206. The calculation of the inner product value P(0) is expressed by the following equation 5-3.

$$x(0) = (x_{\lambda,1}(0), x_{\lambda,2}(0), \ldots, x_{\lambda,m}(0))^T \qquad \text{Eq. 5-1}$$

$$y(0) = (y_{\lambda,1}(0), y_{\lambda,2}(0), \ldots, y_{\lambda,m}(0)) \qquad \text{Eq. 5-2}$$

$$P(0) = x(0) \cdot y(0)^T = x_{\lambda,1}(0) \cdot y_{\lambda,1}(0) + x_{\lambda,2}(0) \cdot y_{\lambda,2}(0) + \ldots + x_{\lambda,m}(0) \cdot y_{\lambda,m}(0) \qquad \text{Eq. 5-3}$$

In the ICA, it is assumed that optical data are an aggregate of independent components. Therefore, when an inner product between the optical data and an independent component is calculated, only a value for that independent component remains and those of other components become 0. Accordingly, the inner product value between the optical data and the independent component is defined as quantitative data of that independent component.

The operating status of the plasma processing apparatus and the processing status of an object being processed are monitored based on changes in the quantitative data such as an inner product value corresponding to each independent component. In case of monitoring the operating status of the plasma processing apparatus, if changes in the quantitative data are small, for example, it is estimated that the plasma is stable. Further, in case of monitoring the processing status of the object being processed, if the inner product value corresponding to each independent component shows a specific change, it is estimated as an end point of etching. In this case, by checking, in advance through, e.g., experiments, the changes in the inner product value corresponding to each independent component depending on the operating status of the plasma processing apparatus and/or the processing status of the object being processed, a reference for decision may be set with the check result showing variation tendencies or singularities. As a consequence, it is possible to check the end point of etching or estimate whether the plasma is stable or not, by merely monitoring the changes in the inner product value corresponding to each emission source; and therefore, the operating status of the apparatus and the processing status of the object being processed can be more simply and accurately monitored.

Figure 9:
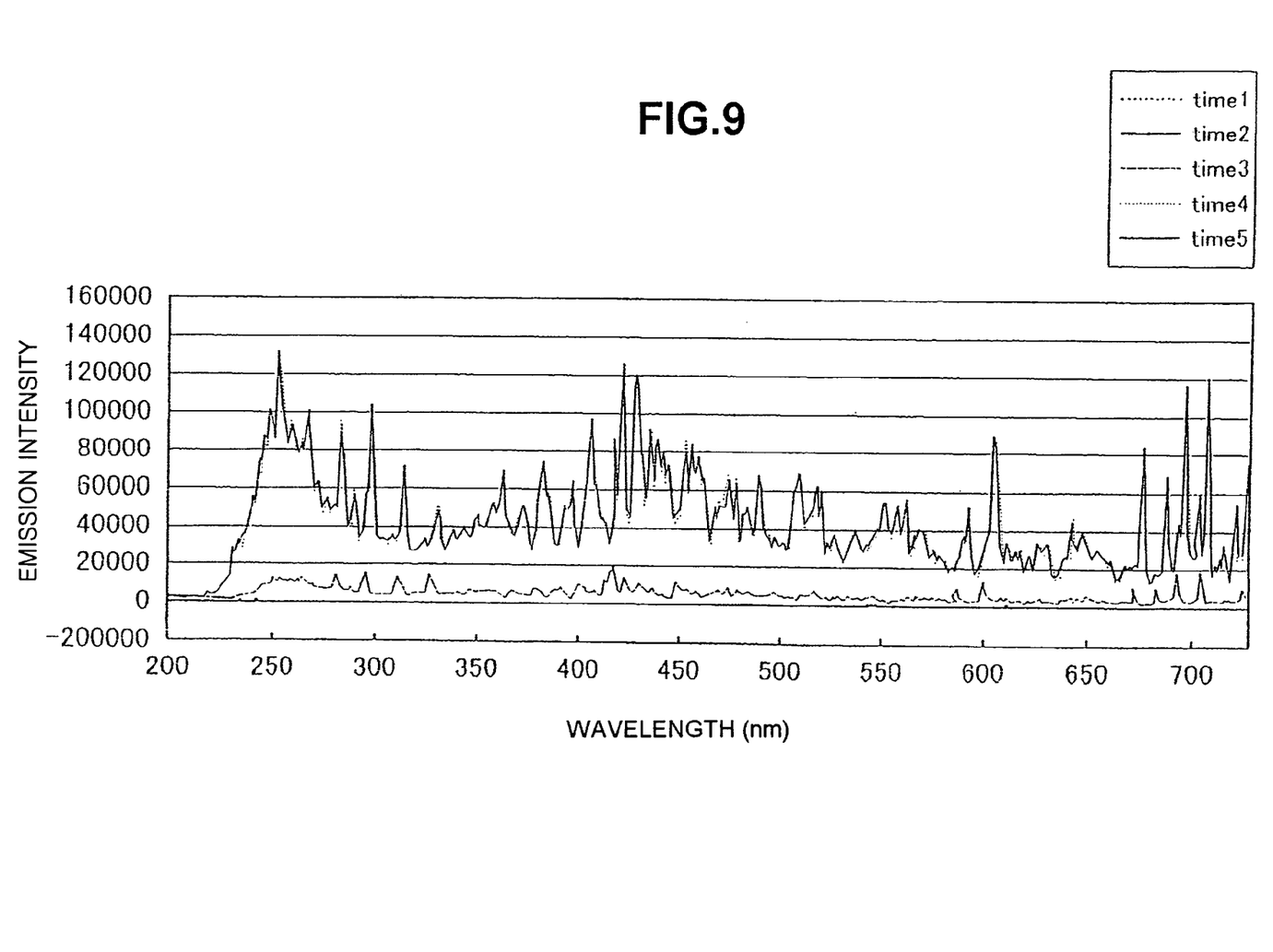
FIG. 9 provides a graph for showing temporal changes in an emission spectrum, which are measured while one piece of wafer is plasma-processed, in the preferred embodiment.

Hereinafter, a specific example of monitoring the operating status of the plasma processing apparatus will be described in detail with reference to the accompanying drawings. FIG. 9 shows optical data obtained at every time interval t by performing a plasma process on a single wafer. Referring to FIG. 9, there are illustrated overall temporal changes in the optical data at representative times, i.e., time 1 to time 5, wherein the X-axis and the Y-axis represent wavelength and emission intensity, respectively. As can be seen from FIG. 9, the emission intensity does not change much at an initial stage after starting the plasma process (time 1 and time 2). The emission intensity then changes a lot (time 3), and becomes stable after a certain period of time (time 4 and time 5).

Figure 10:
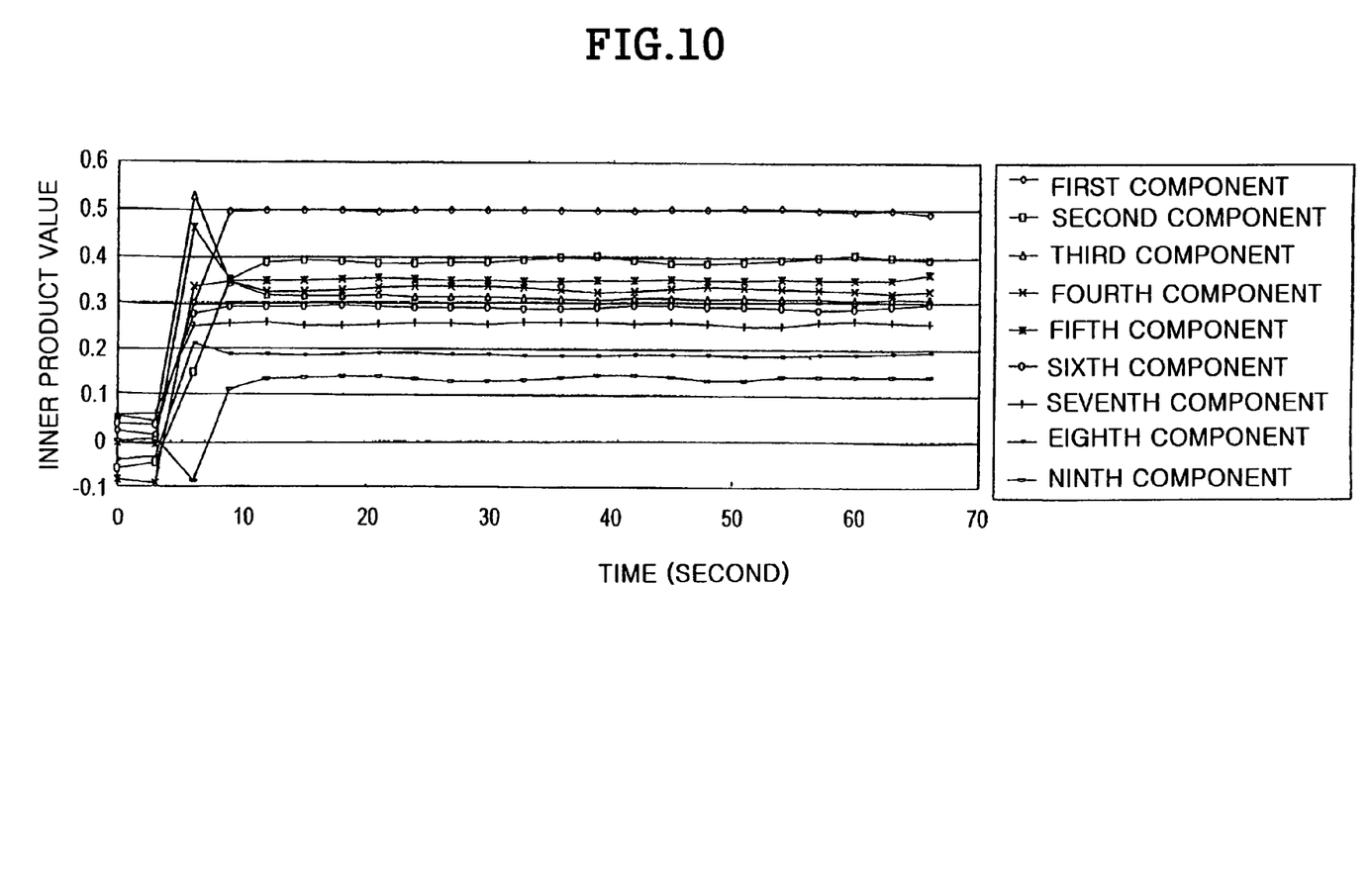
FIG. 10 sets forth a graph for illustrating temporal changes in inner product values corresponding to each independent component in the preferred embodiment.

FIG. 10 offers a graph illustrating inner product values corresponding to each independent component, the inner product values being calculated between the optical data obtained at every time interval t by performing the plasma process on a single wafer and each independent component stored in the database 206. In FIG. 10, the X-axis and the Y-axis represent time t (second) and the inner product values, respectively. In this example, the number of the independent components was nine. Further, the plasma process involved was an etching of a bare silicon. The etching condition was as follows: A high frequency power applied to the lower electrode 102 was 1500 W; a pressure in the processing chamber 101 was 40 mTorr; a process gas was a mixture gas of $C_4F_8$ of 10 sccm, $O_2$ of 4 sccm, CO of 50 sccm, and Ar of 200 sccm. Moreover, a gap between the upper electrode 104 and the wafer was 27 mm.

Referring to FIG. 10, the inner product values corresponding to the independent components (a first to a ninth component) change considerably for about 12 seconds after the plasma process is started. After 12 seconds, the values thereof become stable. This is because the plasma becomes stable about 12 seconds after the process is started. Thus, the stability of the plasma can be estimated by monitoring the timing when the inner product values corresponding to each independent component become stable.

To be more specific, the estimating unit 216 monitors the inner product values sequentially calculated by the optical data developing unit 214 to check whether a difference between a current inner product value and a following inner product value is less than or equal to a predetermined value. In case the difference is less than or equal to the predetermined value, it is estimated that the plasma in the plasma processing apparatus is stable. Alternatively, a ratio of the current inner product value to the next inner product value is calculated. In case the ratio is estimated to be about 1, it is estimated that the plasma in the plasma processing apparatus is stable. Accordingly, it is possible to simply and accurately detect the end point of etching or estimate whether the plasma in the plasma processing apparatus is stable or not.

In the plasma processing apparatus in accordance with the preferred embodiment, the emission spectrum emitted from the plasma is obtained as optical data by the optical measurement device 120 while a wafer is plasma-processed.

Then, the optical data developing unit 214 of the operation unit 208 obtains quantitative data of each emission source from the optical data by using the reference data in the database 206 storing therein emission spectra of a plurality of emission sources as the reference data. Next, the estimating unit 216 checks the quantitative data of each emission source and estimates the operating status of the plasma processing apparatus 100 and/or the processing status of the object being processed, based on changes in the quantitative data of each emission source.

Since the reference data including the emission spectra of a plurality of emission sources are used, it is possible, e.g., to check an end point of etching and estimate whether or not plasma is stable in a processing chamber of the plasma processing apparatus based on data of wider wavelength range compared with a case merely using data of specific wavelengths. Thus, in case semiconductor devices require finer processing performance, e.g., when a hole of a smaller opening ratio is formed on a semiconductor wafer, it is possible to accurately check the end point of etching and estimate whether or not the plasma is stable in the processing chamber of the plasma processing apparatus, thereby improving the accuracy of monitoring the operating status of the plasma processing apparatus and the processing status of the object being processed.

Since the quantitative data of each emission source are obtained by separating the optical data in which the emission spectra of the emission source are mixed and the quantitative data thus obtained are used for checking the end point of the etching or estimating whether the plasma is stable or not, it is possible to estimate the operating status of the plasma processing apparatus or the processing status of the object being processed without being affected by noises which can be mixed in the optical data, for example. Therefore, it is possible to improve the accuracy of monitoring the operating status of the plasma processing apparatus or the processing status of the object being processed.

Further, since the operating status of the plasma processing apparatus is estimated by using the quantitative data of each emission source, which is determined on the basis of the emission spectra (reference data) stored in a database after obtaining the emission spectrum (optical data) emitted from the plasma during the plasma process, it is possible to estimate the operating state of the plasma processing apparatus and the processing state of the object being processed in real time.

The present invention is not limited to the preferred embodiment of the present invention described with reference to the specific accompanying drawings.

For instance, the plasma processing apparatus 100 is not limited to a parallel plate plasma etching apparatus, but the present invention may be applied, e.g., to a helicon wave plasma etching apparatus, an inductively coupled plasma etching apparatus, and the like. Furthermore, although the preferred embodiment describes the plasma processing apparatus adopting the dipole ring magnet, the present invention is not necessarily limited thereto. In other words, the plasma processing apparatus may generate plasma by applying a high frequency power to a top and a lower electrode without using the dipole ring magnet, for example.

In accordance with the present invention, the plasma processing method and apparatus are capable of improving the accuracy of estimating an operating status of the plasma processing apparatus, e.g., the stability of the plasma, and a processing status of an object being processed, e.g., an end point of etching.

While the invention has been shown and described with respect to the preferred embodiment, it will be understood by those skilled in the art that various changes and modifications may be made without departing from the spirit and scope of the invention as defined in the claims.

What is claimed is:

1. A status monitoring apparatus for monitoring an operating status of a plasma processing apparatus and/or a processing status of an object being processed, based on a result of analyzing light emitted from a plasma generated while the plasma processing apparatus performs a plasma process on the object in a processing chamber, the status monitoring apparatus comprising:
    a unit configured to obtain an emission spectrum emitted from the plasma when the plasma process is performed on the object;
    a unit programmed to obtain quantitative data for each of a plurality of emission sources from the obtained emission spectrum by using reference data in a database having stored therein an emission spectrum for each of the emission sources as the reference data, wherein the unit programmed to obtain the quantitative data determines an inner product value between the emission spectrum obtained by the plasma process and the reference data, and sets the inner product value as the quantitative data; and
    a unit programmed to estimate the operating status of the plasma processing apparatus and/or the processing status of the object being processed, based on changes in the quantitative data for each of the emission sources, wherein the reference data is obtained using an independent component analysis, and the emission spectrum for each of the emission sources correspond to an independent component obtained by the independent component analysis.

2. The status monitoring apparatus of claim 1, wherein the database is created in advance by a unit configured to obtain a set of emission spectra, each emission spectrum of the set being emitted from a plasma during each plasma process performed under various process conditions; and
    a unit programmed to separate the set of emission spectra into the emission spectrum for each of the emission sources by the independent component analysis and to store the separated emission spectrum as the reference data.

3. The status monitoring apparatus of claim 2, wherein the number of independent components obtained by the independent component analysis is greater than or equal to the number of process gas species used in the plasma process.

4. The status monitoring apparatus of claim 1, wherein the database is created by a separate database creating unit other than a plasma processing apparatus for performing an actual plasma process.

5. The status monitoring apparatus of claim 1, wherein the unit programmed to estimate the operating status of the plasma processing apparatus estimates that the operating status of the plasma processing apparatus is stable when the quantitative data for each of the emission sources become stable after the plasma processing apparatus begins to perform the plasma process.

6. The status monitoring apparatus of claim 1, wherein the unit programmed to estimate the processing status of the object being processed estimates a completion of the plasma process for the object based on changes in the quantitative data for each of the emission sources.

7. A status monitoring apparatus for monitoring an operating status of a plasma processing apparatus and/or a processing status of an object being processed, based on a result of analyzing light emitted from a plasma generated while the plasma processing apparatus performs a plasma process on the object in a processing chamber, the status monitoring apparatus comprising:
    means for obtaining an emission spectrum emitted from the plasma when the plasma process is performed on the object;
    means for obtaining quantitative data for each of a plurality of emission sources from the obtained emission spectrum by using reference data in a database having stored therein an emission spectrum for each of the emission sources as the reference data, wherein the means for obtaining the quantitative data determines an inner product value between the emission spectrum obtained by the plasma process and the reference data, and sets the inner product value as the quantitative data; and
    means for estimating the operating status of the plasma processing apparatus and/or the processing status of the object being processed, based on changes in the quantitative data for each of the emission sources, wherein the multivariate analysis used for obtaining the reference data is an independent component analysis, and the emission spectrum for each of the emission source corresponds to an independent component obtained by the independent component analysis.

8. The status monitoring apparatus of claim 7, wherein the number of independent components obtained by the independent component analysis is greater than or equal to the number of process gas species used in the plasma process.

* * * * *